US012496364B2

(12) United States Patent
Sephus

(10) Patent No.: US 12,496,364 B2
(45) Date of Patent: Dec. 16, 2025

(54) PIERCED BODY PART HOLE CLEANING KIT AND METHOD FOR CLEANING

(71) Applicant: Mordena Sephus, Robbins, IL (US)

(72) Inventor: Mordena Sephus, Robbins, IL (US)

( * ) Notice: Subject to any disclaimer, the term of this patent is extended or adjusted under 35 U.S.C. 154(b) by 496 days.

(21) Appl. No.: 18/105,547

(22) Filed: Feb. 3, 2023

(65) Prior Publication Data

US 2024/0261448 A1 Aug. 8, 2024

(51) Int. Cl.
*A61L 2/00* (2006.01)

(52) U.S. Cl.
CPC .................................. *A61L 2/0088* (2013.01)

(58) Field of Classification Search
CPC .................................................... A61L 2/0088
See application file for complete search history.

(56) References Cited

U.S. PATENT DOCUMENTS 4,041,946 A 8/1977 Barton
4,497,402 A 2/1985 Karos
4,636,203 A 1/1987 Emanis et al.
4,798,216 A 1/1989 McCarty et al.
5,183,461 A 2/1993 Hobbs
D346,443 S 4/1994 Franklin
5,302,043 A 4/1994 Velliquette
5,739,168 A 4/1998 Hioki et al.
D401,326 S 11/1998 Powell et al.
5,868,245 A 2/1999 Alt
5,871,091 A 2/1999 Fogle
5,931,845 A 8/1999 Amyette
6,051,172 A 4/2000 Fogle
6,146,398 A 11/2000 Satterfield
6,248,085 B1 6/2001 Scholz et al.
6,312,157 B1 11/2001 Masuda et al.
6,358,221 B1 * 3/2002 Waters ...................... A61L 2/26 606/162
6,589,196 B1 7/2003 Sephus
6,595,939 B2 7/2003 Waters, Sr. et al.
D490,521 S 5/2004 Cooper et al.
7,083,602 B1 8/2006 Jennings
D641,865 S 7/2011 Phillips
8,205,745 B2 6/2012 Murray et al.
8,356,457 B2 1/2013 Murray et al.
10,105,019 B2 10/2018 Moore
2002/0192402 A1 12/2002 Parker
2003/0195543 A1 10/2003 Danno
(Continued)

OTHER PUBLICATIONS

Amazon purchase webpage, “Disposable Ear Floss for Ear Hole Piercing Aftercare, Flexible Earrings Hole Cleaner, Pierced Ears Cleaning Line, Gentle Ear Flossing with Rose Fragrance, Odor Removal”, retrieved on Feb. 2, 2023 from https://www.amazon.com/Disposable-Piercing-Aftercare-Flexible-Fragrance/dp/B091PVHQ29, 7 pages.

*Primary Examiner* — Donald R Spamer
(74) *Attorney, Agent, or Firm* — Manatt, Phelps & Phillips, LLP

(57) ABSTRACT

A cleaning kit, device and method are used to clean an old piercing in a body part of a user. The cleaning kit may have a plurality of cleaning elements wherein each cleaning element is sized to clean a particular sixed piercing hole. Each cleaning element may be color coded and may have a gripping point. Each cleaning element may be wetted in a cleaning solution that aids in the cleaning of the old piercing hole.

15 Claims, 8 Drawing Sheets

(56) References Cited

U.S. PATENT DOCUMENTS

| | | | | |
|---|---|---|---|---|
| 2004/0111105 | A1 | 6/2004 | Schmieding et al. | |
| 2005/0165446 | A1 | 7/2005 | Craft | |
| 2007/0143939 | A1 * | 6/2007 | Zocher .................. | A61M 35/00<br>15/104.92 |
| 2011/0092889 | A1 | 4/2011 | Daniels et al. | |

* cited by examiner

PIERCED BODY PART HOLE CLEANING KIT AND METHOD FOR CLEANING

FIELD

The disclosure relates to a pierced hole cleaning kit and more particularly pertains to a new cleaning kit for old pierced holes in a person's body for cleaning and sanitizing the piercing.

BACKGROUND

The use of a pierced hole cleaning kit is known in the prior art. More specifically, a pierced hole cleaning kit heretofore devised and utilized are known to consist basically of familiar, expected and obvious structural configurations, notwithstanding the myriad of designs encompassed by the crowded prior art which have been developed for the fulfillment of countless objectives and requirements.

The various known piercing cleaning kits use some form of a cleaning element that can be passed through the piercing hole to clean the old pierced hole. These known piercing cleaning kits are often saturated with a cleaner that would help to clean the old piercing hole.

While these devices and cleaning kits fulfill their respective, particular objectives and requirements, the cleaning kits do not have a plurality of cleaning elements in which each cleaning element has a different size to clean a different sized piercing hole. Furthermore, these existing cleaning kits do not have color coded cleaning elements that are each color coded to indicate a size of piercing hole to be cleaned by each cleaning element. Furthermore, none of the known cleaning kits have a finger grip on an end of the each cleaning element that allows the user to more easily grip/hold the cleaning element during the cleaning of the old pierced hole.

In these respects, the cleaning kit, device and method for old pierced holes in a person's body substantially departs from the conventional concepts and designs of the prior art and in so doing provide an apparatus primarily developed for the purpose of cleaning and sanitizing pierced holes of a person's body.

DETAILED DESCRIPTION OF ONE OR MORE EMBODIMENTS

The disclosure is particularly applicable to a cleaning kit and method for old pierced ear holes and it is in this context that the disclosure will be described. It will be appreciated, however, that the kit, device and method has greater utility since it can be used to clean old pierced holes in other body parts such as belly buttons, tongues, eyebrows, lips and the like.

Figure 1:
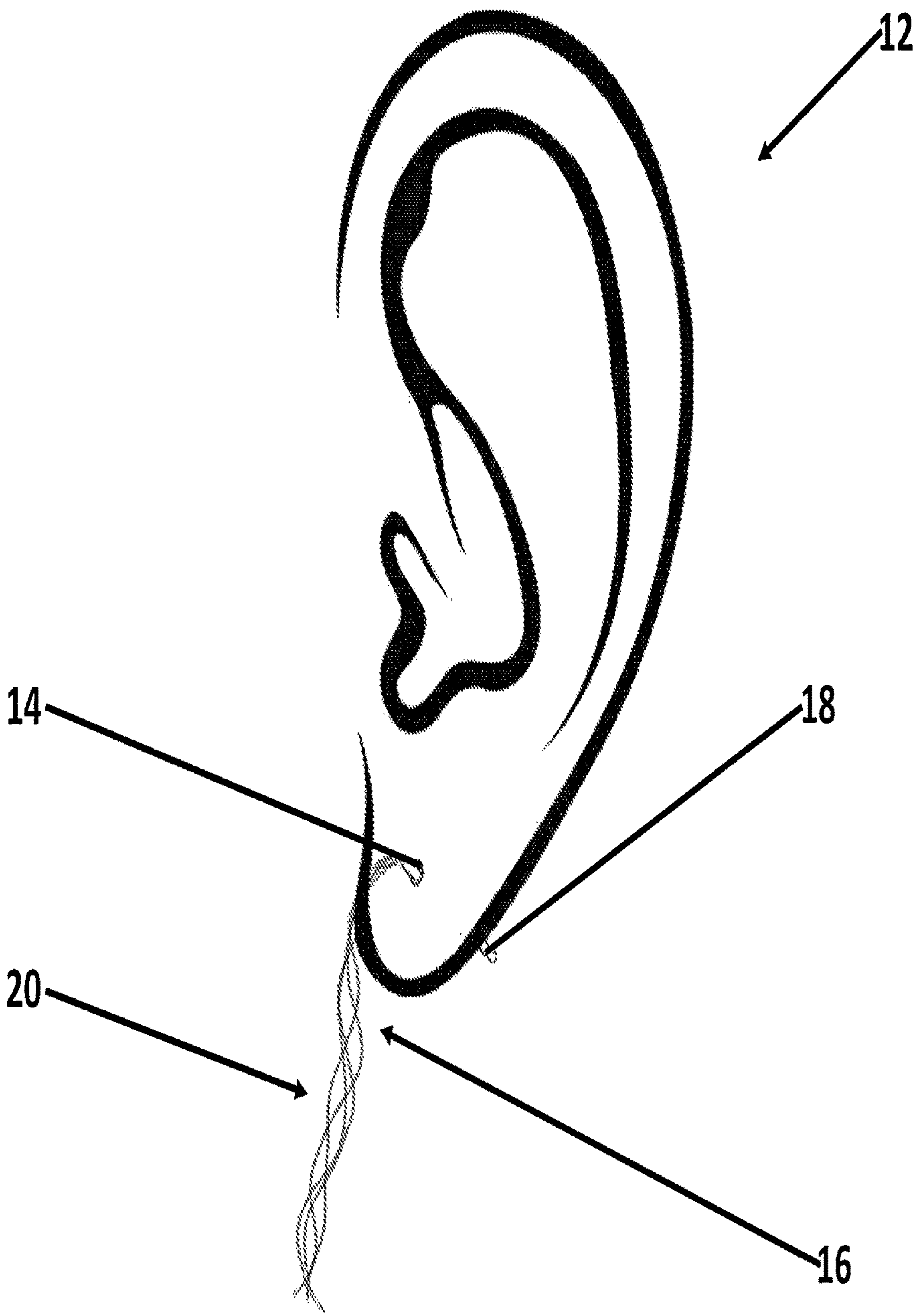
FIG. 1 illustrates a piercing in an ear being cleaned using a cleaning element.

With reference now to the drawings, and in particular to FIGS. 1-7, a new cleaning kit 10 for old pierced holes in a person's body will be described. As shown in FIG. 1, a body part 12 of a person has an old piercing hole 14. In the example in FIG. 1, the body part is an ear of the person, but the old piercing may be in any body part of the person. In the example in FIG. 1, a cleaning element 16 has been inserted through the old piercing hole 14 to clean that old piercing hole 14. The cleaning element 16 may have a diameter, d, that is sized to the size of the old piercing hole 14 as discussed below in more detail. The cleaning element 16 may have a handle portion 18 at one end of the cleaning element 16 that is stiff enough to be passed through the old piercing hole 14 to start the cleaning process. The cleaning element 16 may have one or more strands of material 20 at the other end of the cleaning element 16 that together have the diameter, d, for cleaning the old piercing hole 14. In the example in FIG. 1, the cleaning element 16 has four strands that together have a diameter, d, to clean the old piercing hole 14. The cleaning element 16 may be wetted with a cleaning fluid that helps to clean the old piercing hole 14. For example, the cleaning fluid may be an equal blend of purified water and 0.06% Benzalkonium chloride. Alternatively the cleaning fluid may be warm water, saline water or witch hazel or witch-hazel infused water, perineal solution for intimate areas or any chemical free, hypoallergenic skin care solutions for sensitive skin. As an example, if the cleaning element 16 is being used to clean a piercing in the tongue, warm water may be used as the cleaning fluid. When a cleaning is to be performed, the cleaning element may be wetted with the cleaning fluid selected by the user and the amount of wetting of the cleaning element may be chosen by the user. For example, the cleaning element 16 may be slightly wetted or completely saturated.

Figure 2:
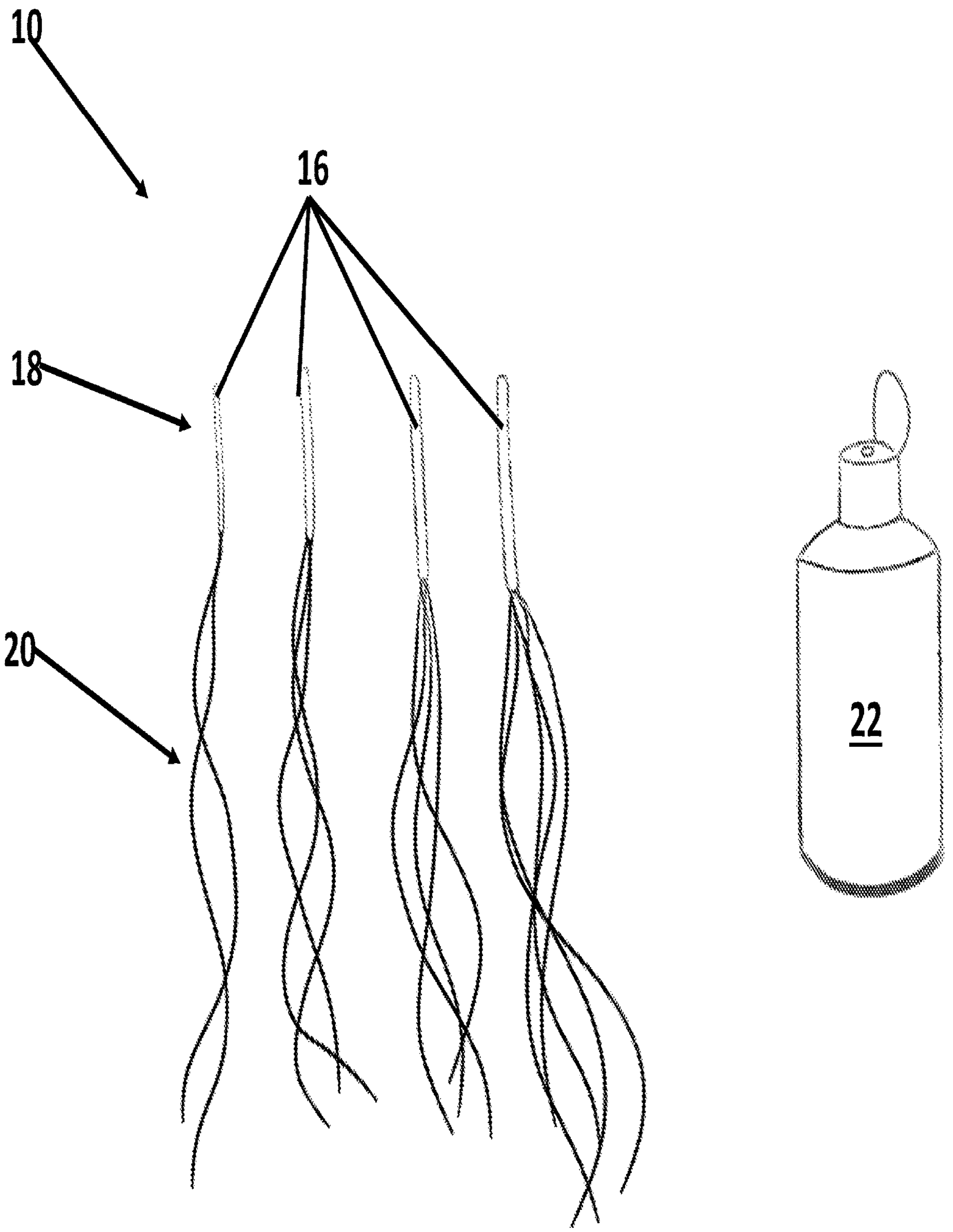
FIG. 2 illustrates a first example of a cleaning kit for old piercings.

FIG. 2 illustrates a first example of a cleaning kit 10 for old piercings that has a plurality of individual cleaning elements 16 (four cleaning elements in this example) wherein each cleaning element 16 has the handle portion 18 and the body portion 20 connected to the handle portion 18. In this example, the individual cleaning elements 16 may have from 2 to 5 strands of material so that, as described above, each cleaning element may have a different diameter for cleaning different sized piercing holes formed by the different sized piercing needles. The cleaning solution may be in a container 22 that is part of the cleaning kit and the cleaning solution may be applied to body 20 of the cleaning element 16 just before a particular cleaning element is used to clean an old piercing hole in a body part. Each strand in each cleaning element 16 may be made with any soft and absorbent fibrous materials, like disposable wipes for sensitive skin or medical gauze cut into graduated strips. An one example, each strand may be made using a DMC six stranded (thread count) of soft and absorbent, 100% white cotton embroidery floss that may be separated into the bunches of strands (1, 2, 3, 4, 5 and then added new strands for thicker piercing needles as shown in the table in the disclosure) for each different sized cleaning element 16. Alternatively, each cleaning element strand/thread may be made from rice paper, silk strands or satin strands. In the various embodiments, each strand may be cut to 6.5 inches long. Each handle portion 18 may be 1 inch to 1.5 inches long and be used to hold the cleaning element 16 and allows the cleaning element to be inserted through the piercing hole. Once the cleaning element is inserted into the piercing hole, the cleaning element 16 may be moved while in the piercing hole to clean it such as by massaging the interior surfaces of the piercing hole 14 with the cleaning element 16. Once used, each cleaning element 16 is disposable.

Figure 3:
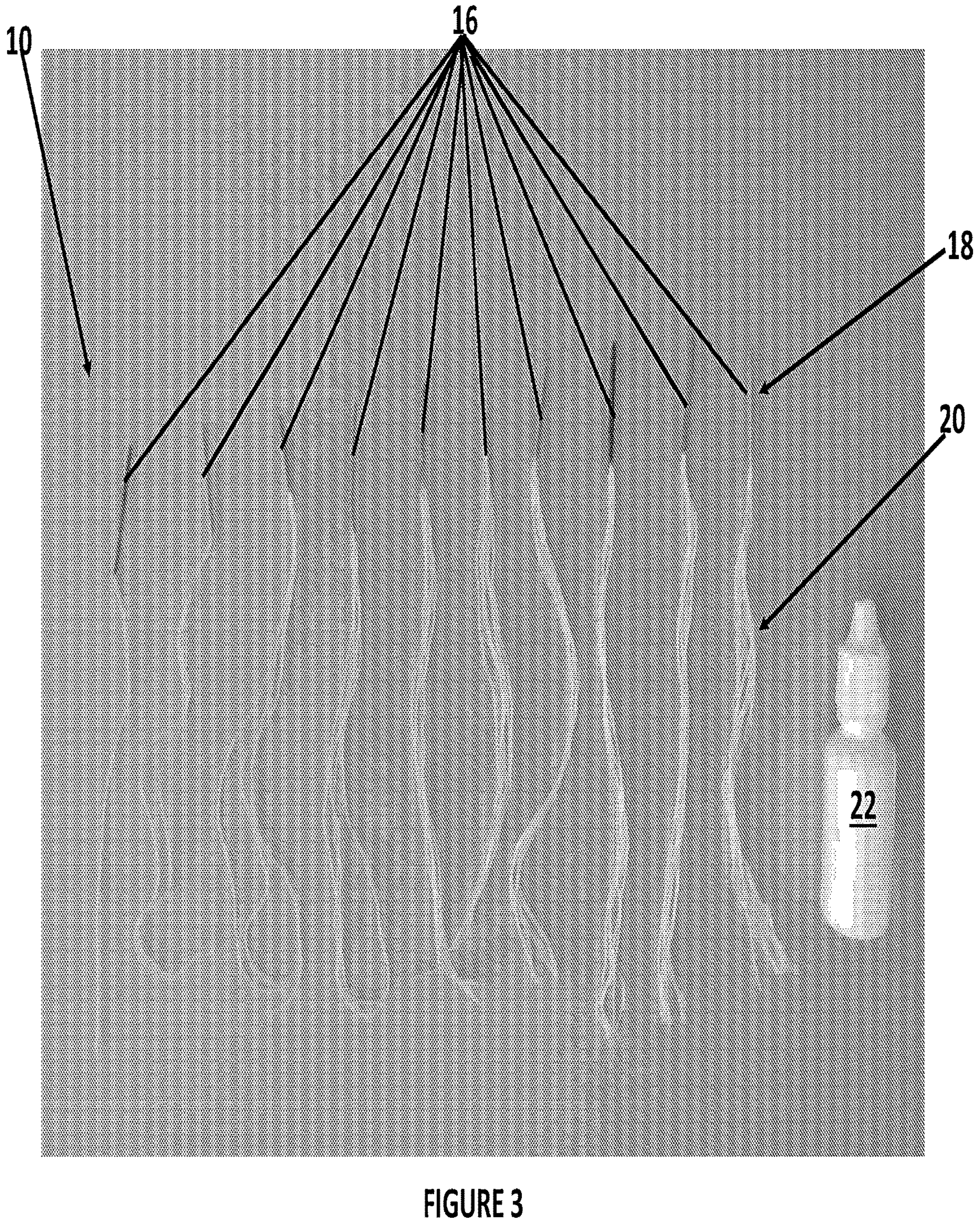
FIG. 3 illustrates a second example of a cleaning kit for old piercings.

FIG. 3 illustrates a second example of a cleaning kit 10 for old piercings that has the same plurality of cleaning elements 16 to clean each size/diameter of piercing hole 14 with the handle portion 18 and body portion 20 (with the one or more strands) and the container 22 of cleaning fluid. In this embodiment, the handle portions 18 may be color coded with different color for the different diameter cleaning elements 16 used to clean the different diameter piercing holes. In one embodiment, the different diameter cleaning elements 16 may be based on a known "Body Piercing Gauge Chart" that shows the different diameter piercing made with different diameter needles. In the Body Piercing Gauge Chart, the largest diameter piercing needle is 00 gauge and thus the largest diameter cleaning element 16 with the most strands may be used to clean a piercing made with the 00 gauge needle. In some embodiments, the diameters of the cleaning materials may range from a 22 gauge needle piercing (extra micro thin) to the 00 gauge needle piercing with the different colors of the color coded handle portions corresponding to the different diameter piercing holes made by the different diameter piercing needles. The multiple diameter cleaning elements and the color coding allows a user to select the appropriate cleaning element for the particular piercing of the person. In this embodiment with the color coded tips of each cleaning element 16, a 7 mm pierced earring sleeve may be but to 1 to 1.5 inches long are glued over the color coded areas using a chemical free bond/glue.

In one embodiment, the cleaning kit 10 may include a plurality of cleaning elements 16 that may range in strand/thread count and have the following color coding for various different sized piercing needle gauges:

| Piercing Needle Gauge | Strand/Thread Count | Color Code |
|---|---|---|
| 22 - Extra Micro Thin | 1 strand/thread count | Purple |
| 20 - Micro Thin | 2 strand or thread count | Lavender |
| 18 - Extra Thin | 3 strand or thread count | Pink |
| 16 - Thin | 4 strand or thread count | Light Blue |
| 14 - Medium | 5 strand or thread count | Green |
| 12 - Thick | 6 strand or thread count | Yellow |
| 10 - Extra Thick | 7 strand or thread count | Grey |
| 8 - 2X Thick | 8 strand or thread count | Blue |
| 6 - 3X Thick | 9 strand or thread count | Red |
| 4 - 4X Thick | 10 strand or thread count | Orange |
| 2 - 5X Think | 18 strand or thread count | Dark grey |
| 00 - 6X Think | 24 strand or thread count | Light Green |

Figure 6:
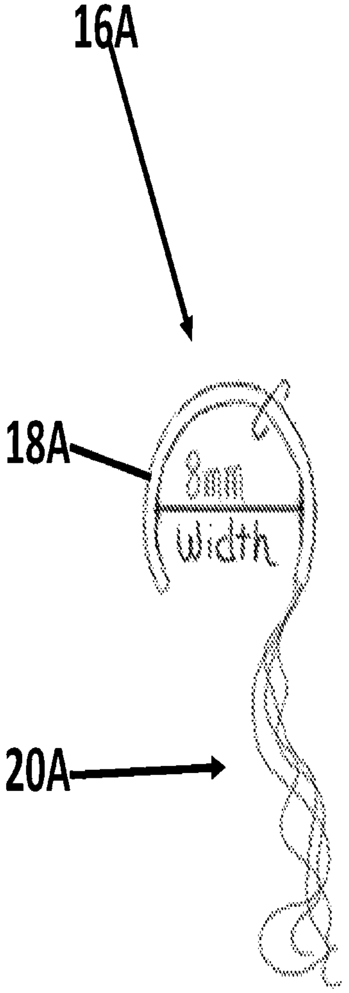
FIG. 6 illustrates an example of a 16 gauge curved cleaning element for a piercing formed using a 16 gauge (1.2 mm) piercing needle.
Figure 7:
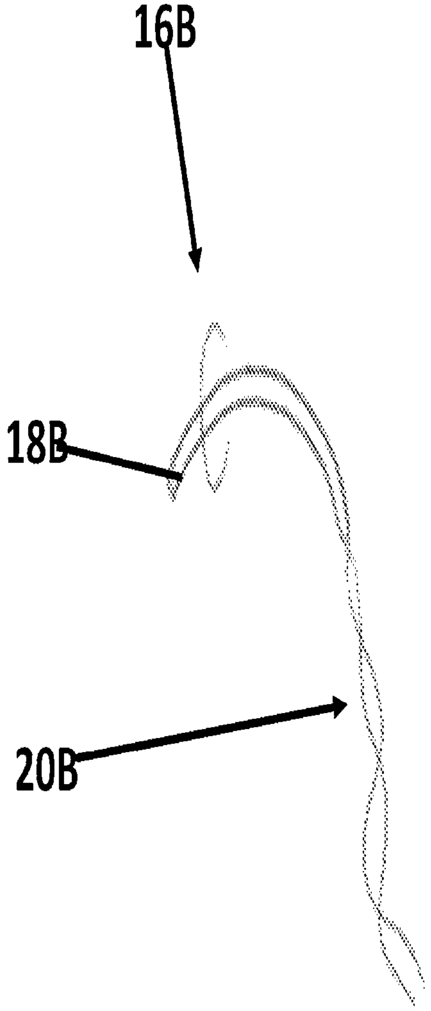
FIG. 7 illustrates an example of a 20 gauge curved cleaning element for a piercing formed using a 20 gauge (0.64 mm) piercing needle.

The cleaning kit for old piercing holes may be at least two cleaning elements having different diameters to clean different diameter piercing holes, may be more than two cleaning elements having different diameters to clean different diameter piercing holes and/or may be a different diameter cleaning element for each gauge of piercing needle on the body piercing gauge chart as shown above. The cleaning kit may also have the plurality of cleaning elements described above along with one or more curved cleaning elements (examples of which are shown in FIGS. 6-7) that may be used to clean piercing holes formed using a curved piercing needle such as a piercing needle used for a belly button (navel), nipple or eyebrow piercing. If there are multiple sizes of curved piercing needles, the cleaning kit may have a cleaning element for each different diameter curved piercing needle such as shown in FIGS. 6-7.

In one embodiment, to achieve the thicker sizes, additional single strands are added to the initial 6 strand embroidery floss. Furthermore, the 1" and 1½" color-coded tips with the sleeve coverings have smooth edges for easy insertion, firmness for push ability as well as flexibility which is adapted to follow along the curvature throughout the inner walls of the pierced skin/holes when pushed through with effortless ease, like that of a tiny medical catheter. In some embodiments, each cleaning element may have a chemical free hand molding multi color "Polly Plastic" to smoothly coat the thicker/larger strands along 1" and 1½" tip. The extended end of the 100% white cotton threading floss/strands, that are not tinted & covered with the piercing sleeves or molding plastic, are 5" to 5½" long and are of multiple thread counts that ranges from the thinnest, 22 gauge, a 1 thread count and continues upwards to 3, 4, 5, 6 and 7+ thread counts, etc., this accommodates the smallest of piercings, up to the largest piercings which matches the most commonly known piercing gauge charts.

The tip portions 18 on the handle of the cleaning element 16 may be flexible, but firm so that it has enough rigidity to be pushed through the piercing hole but is flexible and smooth enough to not damage the tissues on an inner wall of the piercing hole. Furthermore, the tip portions 19 are not sharp so that the tips don't damage the piercing hole tissue during passage through the piercing hole 14. In the case of the curved cleaning element for a curved piercing needle, the tip portion 18 may be curved.

When cleaning a piercing hole, the cleaning fluid wetted cleaning element with the absorbent moistened strands sweep along the inner walls of aged piercings when pulled through, exfoliating and collecting onto the stands upon exiting are, dead skin cells, odor causing bacterial matter, germs, pollutants, minimizing keloids that are associated with some piercings, eliminates pungent odors, removes irritants, cleanses oxidation inside aged piercings that are usually caused from wearing costume jewelry. The cleaning may also eliminate infections, remove body sweat, makeup, shampoos and soap residue. Most piercings remain clean for 2-3 weeks at a time. The cleansing solution also neutralizes pungent odors and germs from recently worn, pierced earring posts and any body piercing inserts, stems or hooks.

For illustration purposes, FIGS. 1-3 show the individual strands of the cleaning element 16. However, the wetting or saturation of the cleaning element causes the strands to stick together so that the wetted cleaning element 16 in FIG. 1 (wetted before being inserted through the piercing hole) would be one piece with the wetted together strands that would have a diameter that is similar to the piercing hole 14.

Figure 4:
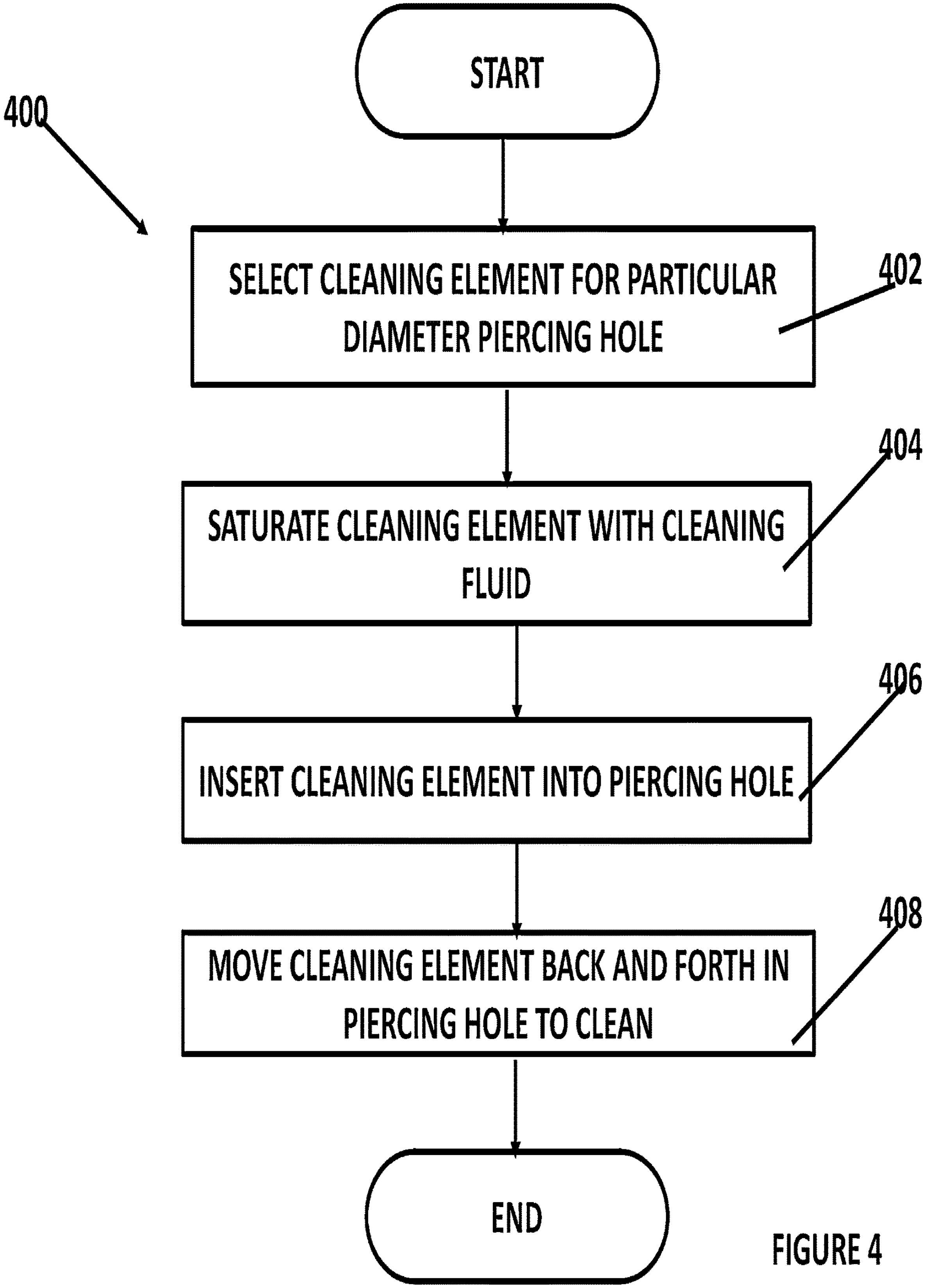
FIG. 4 is a flowchart of a method for cleaning old piercing holes.

FIG. 4 is a flowchart of a method 400 for cleaning old piercing holes that may be performed using the cleaning kits 10 shown in FIGS. 2-3. To start cleaning a piercing, a person determines the diameter of the piercing hole (for example using the Body Piercing Gauge Chart) and then selects the particular sized cleaning element (402) that can clean the particular diameter of piercing hole. The selected cleaning element may then be wetted with cleaning fluid (404). Using the handle and tip, the cleaning element may be inserted into the piercing hole (406). The cleaning element may be moved back and forth within the piercing hole (408) which causes the piercing hole (408) to be cleaned. Once the cleaning is completed, the cleaning element may be removed from the piercing hole and discarded.

Figure 5:
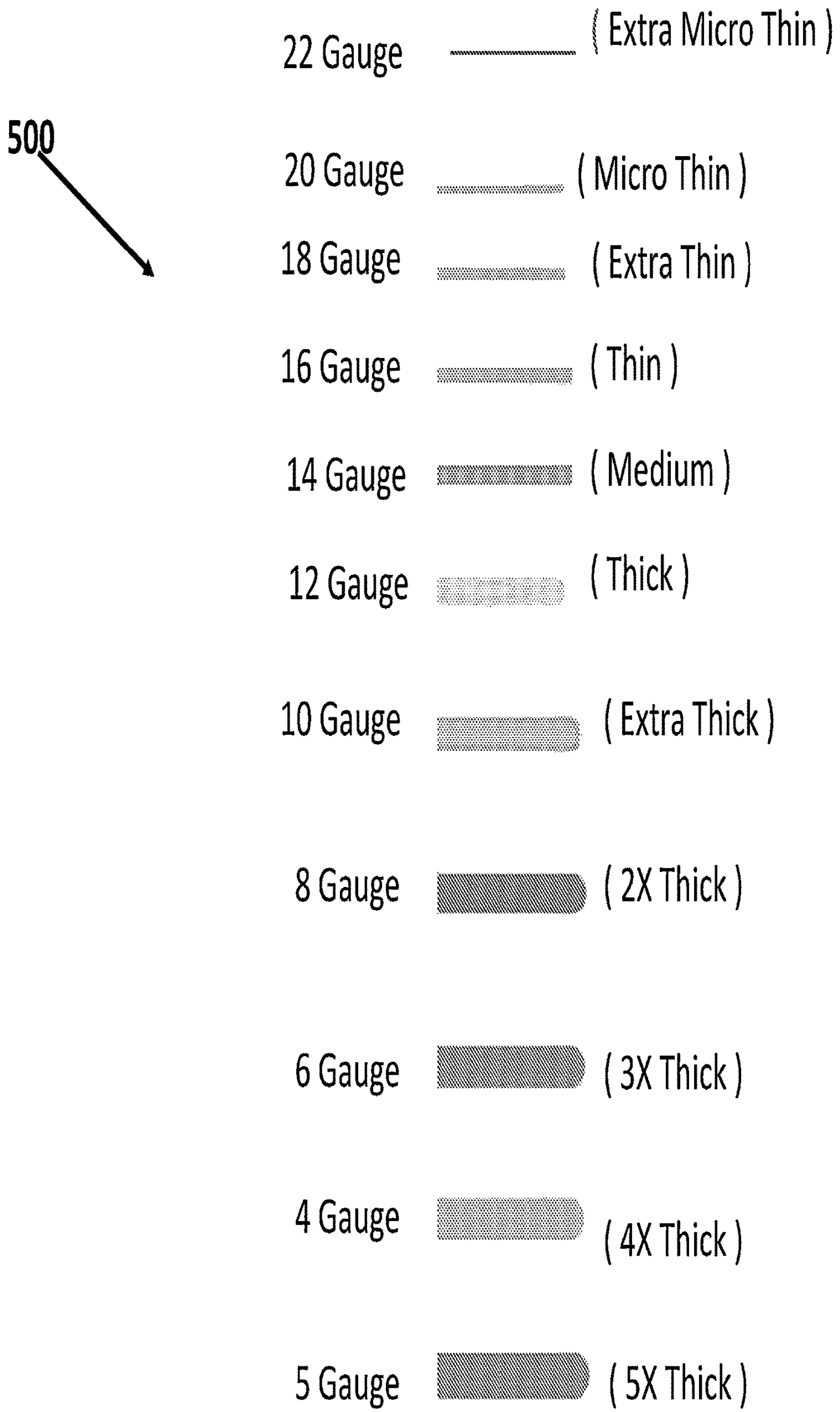
FIG. 5 illustrates an example of a color coded thickness chart that may be included with the cleaning kit to select an appropriate cleaning element.

FIG. 5 illustrates an example of a color coded thickness chart 500 that may be included with the cleaning kit so consumers can more easily select an appropriate cleaning element. For the embodiment of the cleaning kit 10 that has the color handle portions 18, the cleaning kit may include the color chart 500 in FIG. 5 that allows the user to more easily select an appropriate cleaning element for a particular diameter piercing needle. For example, the 22 gauge extra micro thin needle cleaning element 16 may have a purple handle portion 18 while an extra thick 5 gauge cleaning element 16 may have a dark grey handle portion 18. Therefore, once the user knows the gauge of the piercing needle (likely provided to them when they have the piercing performed), the user can then more easily select the appropriate cleaning element diameter based on the color coded thickness chart.

FIG. 6 illustrates an example of a 16 gauge curved cleaning element 16A for a piercing formed using a 16 gauge (1.2 mm) piercing needle and FIG. 7 illustrates an example of a 20 gauge curved cleaning element 16B for a piercing formed using a 20 gauge (0.64 mm) piercing needle. As described above, the cleaning kit may include one or more curved cleaning elements that are used for piercing formed using a curved piercing needle (example body parts in which a curved piercing needle may be used include the eyebrow, a nipple or belly button). The gauge thickness for the curved tips are 12, 14, 16 and 20. The universal size for the curved navel ring and nipple ring is 14 gauge. The standard length is ⅜ inches or 7/16 inch. The gauge size refers to the thickness of the stem going through your body piercing that ranges from 22 G (very thin) to 00 G (thickest). The curved tips are firm and smooth and can be made with medical grade plastic material like a medical catheter or any chemical free plastic coating materials that hardens with firmness, smoothness and has a level of flexibility and push-ability like Putnam Plastics and Smooth-Bor. As shown in FIGS. 6 and 7, the 16 gauge curved cleaning element 16A has the handle portion 18A with a 8 mm width of curvature and the one or more strands 20A used to clean the piercing hole while the 20 gauge curved cleaning element 16B (used to clean a smaller piercing hole (0.64 mm) than the larger piercing hole (1.2 mm) formed by the 16 gauge needle) has the handle portion 18B with less of a curvature and the one or more strands 20B (less strands that the 16 gauge cleaning element 16A since the piercing hole is smaller) used to clean the piercing hole.

Figure 8:
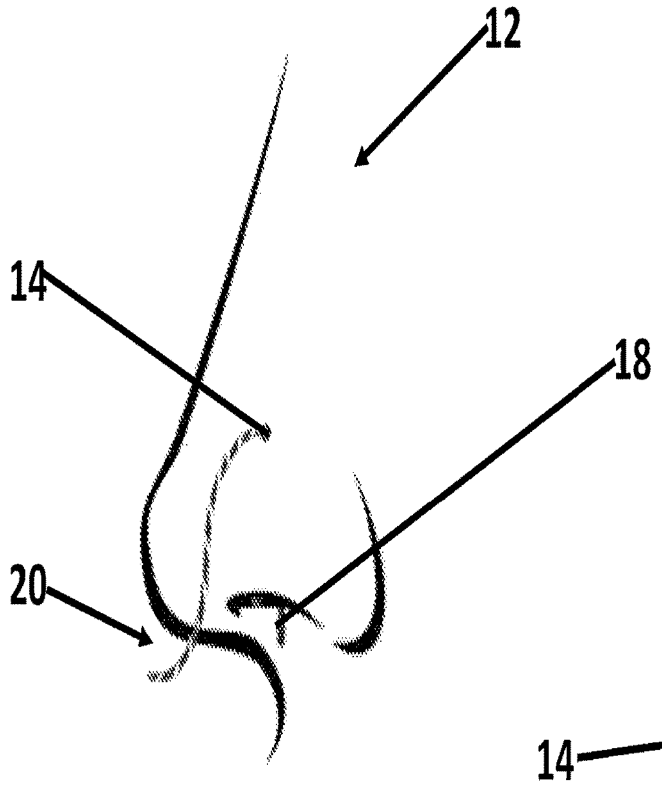
FIG. 8 illustrates a nose piercing being cleaned using a cleaning element.

FIG. 8 illustrates a nose piercing being cleaned using a cleaning element 16 in which the cleaning element 16 in inserted through the piercing hole 14 wherein the cleaning element 16 has the handle portion 18 and the body portion 20. In this figure, the one or more strands of the portion body portion 20 are wetted and thus together unlike the example in FIG. 1. In the example in FIG. 8, a 22 gauge needle (the smallest diameter needle on the piercing gauge chart) was used and the thinnest cleaning element 16 is thus used to clean the piercing hole. A nose piercing may also be done using 18 and 20 gauge needles so a different cleaning element 16 appropriate for a 18 or 20 gauge needle may be used for cleaning the piercing hole.

Figure 9:
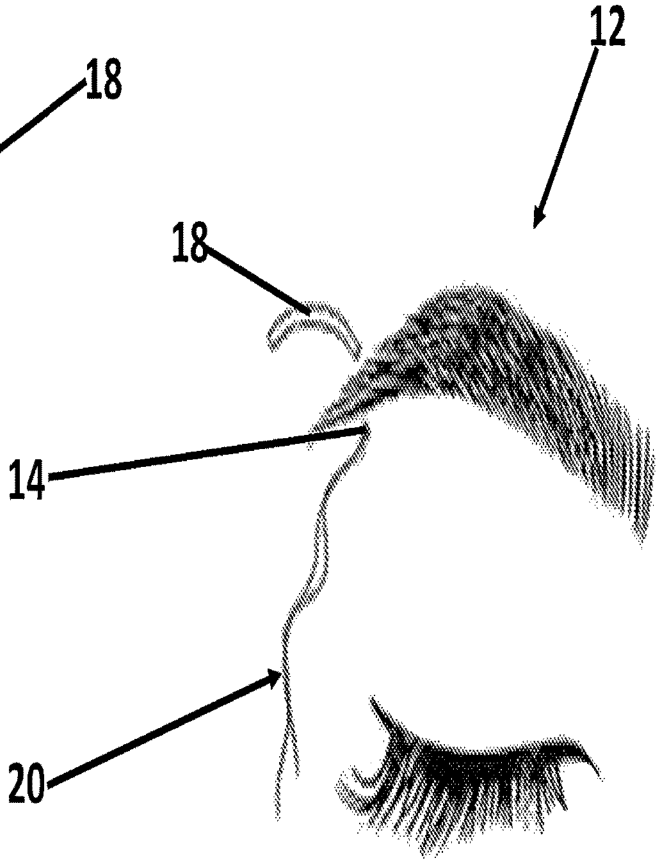
FIG. 9 illustrates an eyebrow piercing being cleaned using a cleaning element.

FIG. 9 illustrates an eyebrow piercing being cleaned using a cleaning element 16 in which the cleaning element 16 in inserted through the piercing hole 14 wherein the cleaning element 16 is curved and has the handle portion 18 and the body portion 20. In this figure, the one or more strands of the portion body portion 20 are shown. In the example in FIG. 9, a 14 gauge needle (1.6 mm) was used and the appropriate cleaning element 16 to clean the piercing hole 14 made by the 14 gauge needle may be used to clean the piercing hole 14. A 16 gauge needle (1.2 mm) may also be used for the eyebrow piercing.

Figure 10:
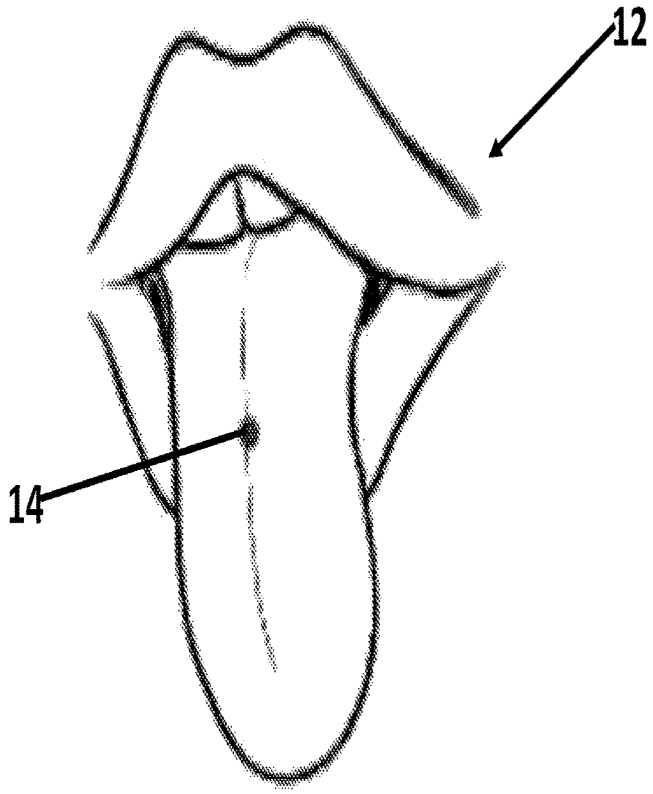
FIG. 10 illustrates a tongue piercing that may be cleaning using a cleaning element.
Figure 11:
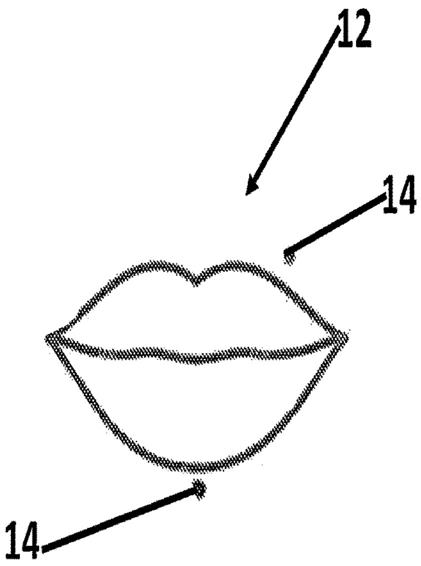
FIG. 11 illustrates a Monroe piercing that may be cleaning using a cleaning element.

FIG. 10 illustrates a tongue piercing that may be cleaning using a cleaning element. The piercing hole 14 in the tongue is shown. The tongue piercing may be made by a 14 gauge needle and the appropriate cleaning element 16 to clean a piercing hole formed by the 14 gauge needle may be used. FIG. 11 illustrates a Monroe piercing that may be cleaning using a cleaning element. The piercing hole(s) 14 adjacent the lips are shown. The Monroe piercing may be made by a 16 gauge needle and the appropriate cleaning element 16 to clean a piercing hole formed by the 16 gauge needle may be used.

The foregoing description, for purpose of explanation, has been with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

What is claimed is:

1. A cleaning kit, comprising:

a plurality of cleaning elements wherein each cleaning element has a diameter for cleaning a particularly sized old piercing hole in a body part, each cleaning element having a handle portion connected to a body portion having two or more strands of material, wherein the number of the strands depends on a diameter of a piercing hole to be cleaned using the cleaning element;

a container of cleaning fluid placeable onto the two or more strands of the body portion to wet the two or more strands of the body portion.

2. The cleaning kit of claim 1, wherein each cleaning element has a color code indicating a size of the piercing hole to be cleaned using each cleaning element.

3. The cleaning kit of claim 2, wherein the plurality of cleaning elements further comprises a cleaning element for cleaning a piercing hole formed by a 100 gauge needle to a cleaning element for cleaning a piercing hole formed by a 22 gauge needle.

4. The cleaning kit of claim 1, wherein each strand is a 100% white cotton embroidery floss.

5. The cleaning kit of claim 1, wherein each strand is one of rice paper, silk and satin.

6. The cleaning kit of claim 1, wherein the plurality of cleaning elements further comprises a cleaning element for each gauge piercing needle on a body piercing gauge chart.

7. The cleaning kit of claim 1, wherein the cleaning fluid includes one of an equal blend of purified water and 0.06% Benzalkonium chloride, an amount of warm water, an amount of saline water, a witch hazel infused liquid, and a perineal solution.

8. The cleaning kit of claim 1 further comprising at least one cleaning element being curved to clean a piercing hole formed by a curved piercing needle.

9. The cleaning kit of claim 1 further comprises a color coded gauge thickness chart.

10. A cleaning element, comprising: a handle portion; a body portion connected to the handle portion, the body portion having a plurality of strands wherein a number of the plurality of strands depends on a diameter of a piercing needle used to form a piercing hole to be cleaned using the cleaning element; the handle portion having a color that indicates the diameter of a piercing needle that forms the piercing hole; and the body portion being wetted with a cleansing fluid to aid in the cleaning of the piercing hole.

11. The cleaning element of claim 10, wherein each strand is one of white cotton embroidery floss, rice paper, silk and satin.

12. The cleaning element of claim 10, wherein the cleansing fluid includes one of an equal blend of purified water and 0.06% Benzalkonium chloride, an amount of warm water, an amount of saline water, a witch-hazel infused liquid, and a perineal solution.

13. A method for cleaning for old piercing hole, the method comprising:

determining a diameter of an old piercing hole in a body part;

selecting, based on the determined diameter of the old piercing hole, a particular cleaning element of a cleaning kit, the selected particular cleaning element being selected from a plurality of cleaning elements each having two or more strands of material that together have a diameter that is similar to the diameter of the old piercing hole;

wetting the selected particular cleaning element with a cleaning fluid;

inserting the wetted cleaning element through the old piercing hole; and cleaning the old piercing hole using the wetted cleaning element.

14. The method of claim 13, wherein selecting the particular cleaning element further comprises using a color coded gauge thickness chart to select the particular cleaning element.

15. The method of claim 13, wherein wetting the body portion of the selected cleaning element further comprises wetting the body portion of the selected cleaning element with a cleaning liquid including one of an equal blend of purified water and 0.06% Benzalkonium chloride, an amount of warm water, an amount of saline water, a witch hazel infused liquid, and a perineal solution.

* * * * *